United States Patent [19]

Popescu

[11] Patent Number: 5,822,393
[45] Date of Patent: Oct. 13, 1998

[54] METHOD FOR ADAPTIVELY MODULATING THE POWER LEVEL OF AN X-RAY TUBE OF A COMPUTER TOMOGRAPHY (CT) SYSTEM

[75] Inventor: Stefan Popescu, Bukarest, Romania

[73] Assignee: Siemens Aktiengesellschaft, Munich, Germany

[21] Appl. No.: 831,411

[22] Filed: Apr. 1, 1997

[51] Int. Cl.⁶ .................................................. H05G 1/20
[52] U.S. Cl. ............................ 378/108; 378/16; 378/145
[58] Field of Search .............................. 378/16, 146, 108, 378/109, 110, 111, 112, 145

[56] References Cited

U.S. PATENT DOCUMENTS 5,379,333  1/1995  Toth .......................................... 378/16
5,400,378  3/1995  Toth .......................................... 378/16

*Primary Examiner*—Don Wong
*Attorney, Agent, or Firm*—Hill & Simpson

[57] ABSTRACT

In a method for adaptively modulating the power level of an x-ray tube of a computer tomography (CT) system for reducing an x-ray dose of an x-ray beam radiating through a patient and reaching detector means of said CT system during the acquisition of projections of body slices of the patient, the value of the maximum attenuation level per projection is established out of the patient projection data acquired for the respective projection and stored in a memory. The value of the maximum attenuation level for the next projection is predicted based on at least one of the stored values of the maximum attenuation levels and the respective power level of the x-ray tube for the next projection is established. Finally the respective power level of the x-ray tube for the next projection is accordingly adjusted.

8 Claims, 2 Drawing Sheets

METHOD FOR ADAPTIVELY MODULATING THE POWER LEVEL OF AN X-RAY TUBE OF A COMPUTER TOMOGRAPHY (CT) SYSTEM

BACKGROUND OF THE INVENTION

1. Field of the Invention

The present invention relates to computed tomography (CT) imaging; and more particularly, to a method for reducing an x-ray dose of an x-ray beam radiating through a patient during the computed tomography (CT) imaging without significantly increasing noise artifacts in the final image.

2. Description of the Prior Art

In general a conventional computed tomography system comprises as main elements an x-ray source, a bank of x-ray detectors and a patient table. The x-ray source and the bank of detectors are placed on a gantry that rotates around the patient table. Normally, the patient table can be moved relative to the gantry. The x-ray source produces a collimated, fan-shaped x-ray beam. This x-ray beam passes through a slice of a object being imaged, such as a patient, who is lying on the patient table, and impinges upon the bank of x-ray detectors. The angle at which the x-ray beam intersects a body slice of the patient and possibly the position of the patient table relative to the gantry is/are continuously changed during CT imaging.

The intensity of the transmitted x-rays striking on the bank of x-ray detectors is dependent upon the attenuation of the x-ray beam by the patient. Thus each detector of the bank of detectors produces a voltage signal that is a measurement of the body's global transparency from the x-ray source down to the respective detector. The set of detector voltage signals, i. e. attenuation data, acquired for a particular x-ray source position relative to the patient is referred to as a "projection" and a set of projections made at different gantry positions during revolution of the gantry around a patient is referred to as a "scan". By the way, for every projection a monitor detector of the bank of detectors measures the unattenuated x-ray beam intensity which is used to normalize the voltage values of the detector voltage signals and to establish the global attenuation. The CT system acquires many projections at different positions of the x-ray source relative to the body of the patient in order to construct an image that corresponds to a two dimensional section taken through the body of the patient or to a 3D image. The prevailing method for reconstructing an image from acquired attenuation data is referred to in the art as the filtered backprojection technique.

The quality of the reconstructed image of a body slice of the patient is first of all affected by the quantum noise which is related to the amount of x-ray dose employed to acquire the attenuation data, and to the attenuation characteristics of the patient. Image artifacts due to noise will increase if the x-ray intensity measured at the bank of detectors drops to low levels either because the applied x-ray dose is too low or the x-ray beam is highly attenuated by patient anatomy. In order to keep the detector voltage signals above the noise for every projection, the momentary x-ray power level of an x-ray tube has to be great enough so that the minimum intensity of an x-ray beam applied to a patient leaving the body of the patient and reaching the bank of detectors is greater than the noise level of the detectors. Nevertheless, the x-ray power level of an x-ray tube for every projection should be as low as possible in view of the total x-ray exposure to the patient. That is the reason why it is necessary to modulate the x-ray power level during the acquisition of patient projection data, wherein modulating the x-ray power level of an x-ray tube means modulating the intensity of an x-ray beam emitted by an x-ray tube.

Most of the conventional methods that modulate the x-ray power level during the CT scan to adapt the x-ray power level to the actual to be examined anatomical domain of the patient used until now need a pre-scan or a scout-scan in order to acquire some information regarding an attenuation profile of a body slice of a patient, wherein the attenuation profile is the maximum attenuation per projection as a function of the gantry angle. A pre-scan for example is done with constant x-ray intensity in order to compute and store an attenuation profile for a complete slice. This information is used for the power modulation process in the next successive slice. This method is adequate for example for spiral exploration mode, i. e. multiple rotation of the gantry and simultaneous translation of the patient table in a direction substantially perpendicular to the plane of the fan shaped x-ray beam, of a CT system, when successive slices are close enough and the attenuation profile is supposed to be nearly identical from one slice to the next, but includes also the drawback of a increased x-ray exposure to the patient. Moreover, when the translation speed of the patient table is high, or when the distance between successive slices is large, the accuracy of this procedure is insufficient. In single slice exploration mode of a CT system conventional methods, for example the method described in U.S. Pat. No. 5,379,333, require normally at least two orthogonal projections (scout-scans) of a body slice of a patient to be carried out in order to build a power modulation profile. Also these methods still have many drawbacks:

- increased x-ray dose due to extra x-ray exposure used to get the scout projections;
- a weak fit of the computed attenuation profile to the real attenuation profile, due to the fact that the two orthogonal projections do not necessary find the maximum slice's attenuation, especially in examinations involving the administration of contrast medium;
- supplementary patient x-ray dose and not homogeneous noise in the image due to the fact that the attenuation profile does not fit the real attenuation profile;
- patient and/or respiration movements between scout scan and final scan change the attenuation profile and induce extra errors.

SUMMARY OF THE INVENTION

An object of the present invention is therefore to provide a method for a computer tomography system in which the total x-ray dose of an x-ray beam radiating through a patient during the acquisition of patient projection data is kept as low as possible without significantly increasing noise artifacts in the final image with this method working equally well for all common scanning modes: spiral, sequence, rotational and even tomogram. This object is inventively achieved using a method in which the x-ray power level is continuously modulated based on acquired attenuation information. Projections of body slices of the patient are measured and the value of the maximum attenuation level per projection is established. All or some of the established values per projection are stored and based on at least one (or more) of these stored values the value of the maximum attenuation level for the next projection is predicted. Based on this predicted value of the maximum attenuation level the power level of the x-ray tube of the CT system for the next projection is such established and accordingly adjusted that the minimum intensity of an x-ray beam radiating through the patient and reaching detector means of the computer tomography system is greater than the quantum noise of the detector means. I. e. pre- or scout-scans with all their drawbacks are avoided. Thus the x-ray dose of the x-ray beam radiating through the patient during the acquisition of patient projection data per projection is substantially reduced and the total exposure of x-rays radiating through the patient during the whole examination is decreased.

A further object of the invention is to provide a relative fast and simple method for predicting the value of the maximum attenuation level of the next projection. The prediction method uses the maximum attenuation level(s) of the preceding projection(s) in order to find out the most expected value of the maximum attenuation level for the next projection. The simplest and thus preferred method is the so called first order prediction method, that assumes that the value of the maximum attenuation level of the next projection is approximately equal with the value of the maximum attenuation level of the last projection:

$$A_{max\_pred}(t) = A_{max\_real}(t-1),$$

wherein $A_{max\_pred}(t)$ is the predicted value of the maximum attenuation level of the next projection, and $A_{max\_real}(t-1)$ is the established and stored value of the maximum attenuation level of the foregoing projection.

Also the so called second order linear prediction method can be used. This method uses only the maximum attenuation levels of the last two projections in order to predict the value of the maximum attenuation level of the next projection:

$$A_{max\_pred}(t) = 2 A_{max\_real}(t-1) - A_{max\_real}(t-2),$$

wherein $A_{max\_pred}(t)$ is the predicted value of the maximum attenuation level of the next projection, $A_{max\_real}(t-1)$ is the established and stored value of the maximum attenuation level of the foregoing projection, and $A_{max\_real}(t-2)$ is the established and stored value of the maximum attenuation level of the last but one projection.

This means that the power level modulation process starts as soon as after one or two projections and, normally, after less than one degree of gantry rotation, whereat for example the SOMATOM Plus 4 CT system of Siemens has in one operating mode a gantry rotating time of 750 ms by a resolution of about 3 projections per degree.

A more specific object of the invention is the definition of a strategy of power modulation. The method uses two input parameters: the desired power density (p), and the maximum power level allowed during a scan. The power density is a parameter that gives the best control on the final image quality. A higher power density will produce a better signal to noise ratio in the final image and thus a better image quality. Based on the predicted value of the maximum attenuation level, the power density and the maximum admissible power level of an x-ray tube for a projection the x-ray power level is such established that the minimum intensity of an x-ray beam radiating through the patient and reaching detector means of the computer tomography system is greater than the quantum noise of the detector means and limited to the maximum allowed power. The value of power density on which the power level modulation is based is chosen as necessary or desired for a good final image quality. A preferred method to establish the power level of an x-ray tube for a respective projection is $$P_{est} = (A_{max\_pred}(t))^{-1} \rho$$

if $(P_{est} > P_{max})$ then $P_{est} = P_{max}$ wherein $P_{est}$ is the established power level of the x-ray tube of the next projection which is to adjust, $P_{max}$ is the maximum admissible power level of the x-ray tube for a projection, $\rho$ is the desired power density, and $A_{max\_pred}(t)$ is the predicted value of the maximum attenuation level of the next projection.

Another object of the invention is to use a different procedure for tube's anode current modulation for adjusting the power level of the x-ray tube of the CT system. The previous methods use the heater temperature modulation in order to indirectly adjust the anode current and thus the power level of an x-ray tube. This leads to a very slow response and thus to a very slow modulation of the x-ray power level and does not allow the necessary speed required to follow up the real attenuation profile. This necessitates additional speed correction procedures that induce three drawbacks: extra computing time, supplementary x-ray dose and noise inhomogenities. These drawbacks become more substantial as the gantry speed is higher. To avoid these drawbacks the invention uses an x-ray tube with a third electrode acting as an electric gate. By modulating the gate to cathode potential according to the established x-ray power level(s) the x-ray power level(s) is/are able to follow the continuously predicted attenuation profile even at high gantry rotation speeds practically without any delay.

DETAILED DESCRIPTION OF THE INVENTION

Figure 1:
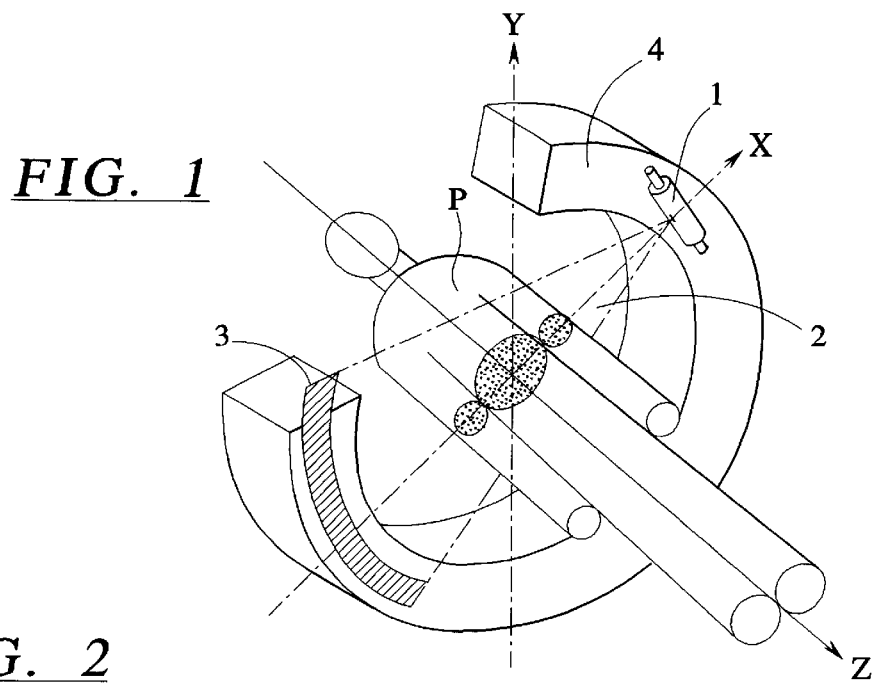
FIG. 1 is a schematic view of a part of a CT imaging system used to build cross section images of body slices of a patient.

FIG. 1 shows in a schematic view a part of a so called third generation CT imaging system comprising as an x-ray source an x-ray tube 1 that emits a fan-shaped x-ray beam 2 toward a bank of for example 768 detectors 3. Both the x-ray tube 1 and the bank of detectors 3 are placed on a gantry 4, which is able to continuously rotate around a patient P, who is lying on a patient table, which extends into the gantry 4 and is not shown in FIG. 1. The gantry 4 rotates in a x-y plane of a Cartesian coordinate system x, y, z shown in FIG. 1. The patient table is movable along the z axis of the Cartesian coordinate system.

Figure 2:
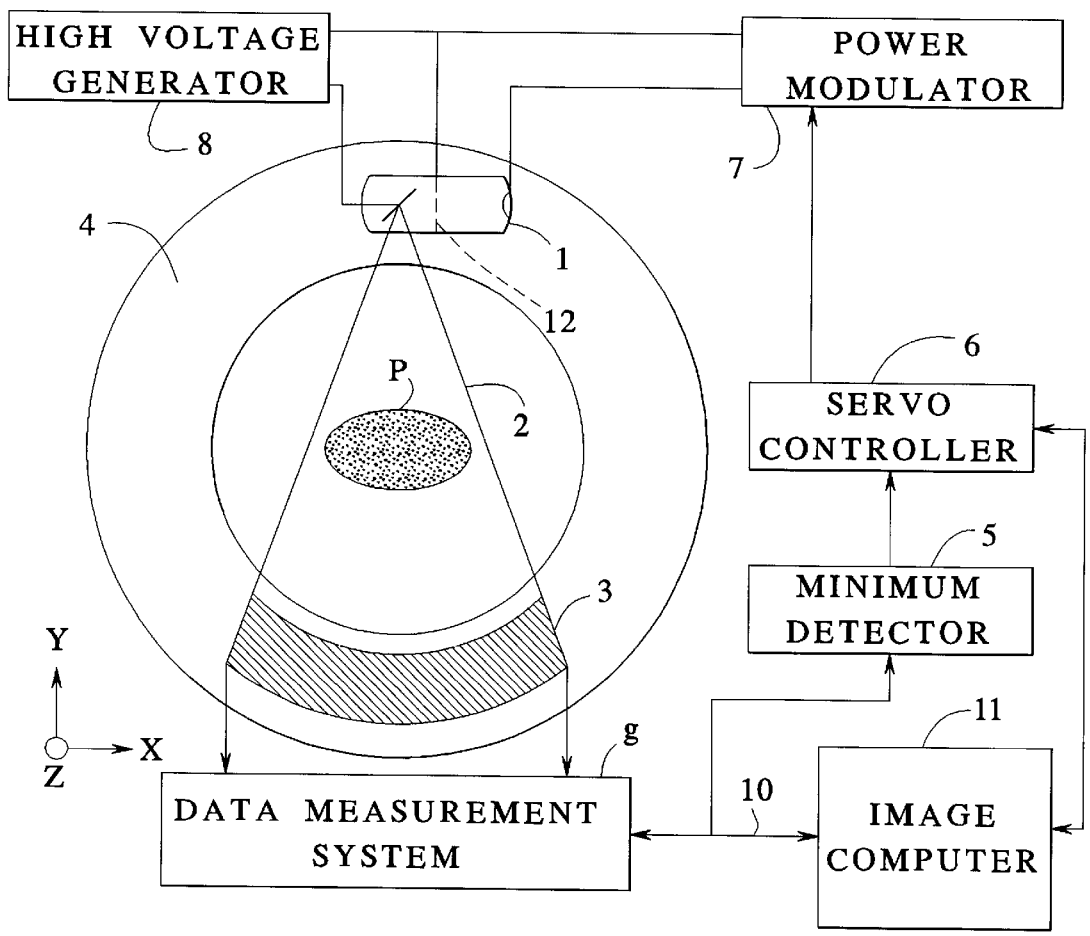
FIG. 2 is a block schematic diagram of a CT imaging system for executing the inventive method.

FIG. 2 shows another view of the third generation CT imaging system of FIG. 1. FIG. 2 is a block schematic diagram showing the system components of a feed-back system for executing the inventive method for adaptively modulating the power level of the x-ray tube 1 to rapidly modulate and reduce the x-ray dose of the x-ray beam 2 radiating through the patient P during the acquisition of patient projection data. The feed-back system comprises a hardware minimum detector 5, a servo controller 6 and a power modulator 7. The feed-back loop of the feed-back system is closed and comprises the x-ray tube 1 with a gate electrode 12 for rapidly modulating the x-ray dose of the x-ray beam 2 radiating through the patient P, the patient P, the bank of detectors 3, a data measurement system 9 and a high speed data link 10. A high voltage generator 8 supplies the x-ray tube 1 with a high voltage of about 120 kV. An image computer 11 is used to reconstruct cross section images of body slices of the patient P based on acquired patient projection data.

Figure 3A:
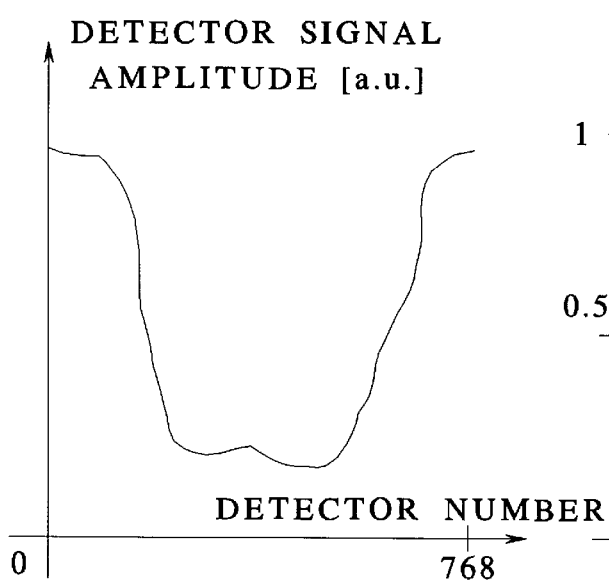
FIG. 3a is a typical signal profile of signals measured at a bank of detectors for one projection of a body slice of a patient.

In operation of the CT imaging system the fan-shaped x-ray beam 2 emitted from the x-ray tube 1 passes through a body slice of the patient P and impinges upon the bank of detectors 3. The detectors of the bank of detectors 3 produces voltage signals at the 768 different detector channels which are sampled by the data measurement system 9. The set of detector voltage signals acquired for a particular x-ray tube 1 position relative to the patient P is referred to as a projection. FIG. 3a shows a typical signal profile for a projection wherein the amplitudes of the detector voltage signals are represented in a arbitrary unit as a function of the detector number. As a matter of fact the CT imaging system acquires many projection, i.e. up to 1000 projections and more, per revolution of the gantry 4 around the patient P, in order to be able to reconstruct a cross section image of a body slice of the patient P by applying the filtered back-projection technique which is known in the art and which is substantially performed by the image computer 11. The reconstructed images are, normally, represented on a monitor not shown in FIG. 2 which is connected to the image computer 11.

For every projection during the acquisition of patient projection data the detector of the bank of detectors 3 that receives the lowest x-ray intensity records the minimum voltage signal and thus the maximum attenuation for this projection. It is the output voltage signal of this detector that is most sensitive with regard to both quantum and electronic noise. In order to keep the output voltage signal of this detector above the noise level, it is therefore necessary to set the power level of the x-ray tube 1 for a respective projection just great enough so that the minimum intensity of the x-rays that reach the bank of detectors 3 is greater than a prescribed level that makes sure that the output voltage signal of the detector representing the minimum x-ray intensity is above the noise level. Only in this case the measured detector voltage signals are usable for reconstructing a noise free cross section image of the patient P.

The CT imaging system also comprises a reference detector (monitor channel or monitor detector) which measures for every projection the unattenuated x-ray intensity, and the voltage signal measured at this detector is used to establish the global attenuation at every other detector of the bank of detectors 3.

Figure 3B:
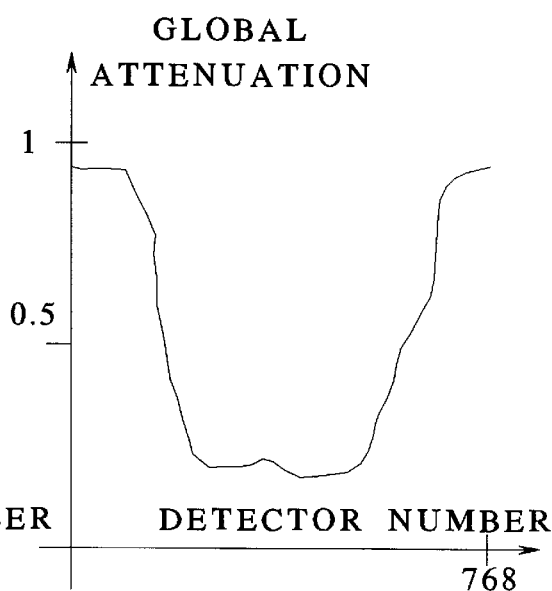
FIG. 3b is a signal profile of the x-ray attenuation for one projection of a body slice of a patient.

FIG. 3b shows a typical signal profile of the global attenuation established for a measured projection wherein the established values of the global attenuation are represented as a function of the detector number. The attenuation value 0 of a detector of the bank of detectors 3 means that there were no x-rays incident on this detector.

Figure 4A:
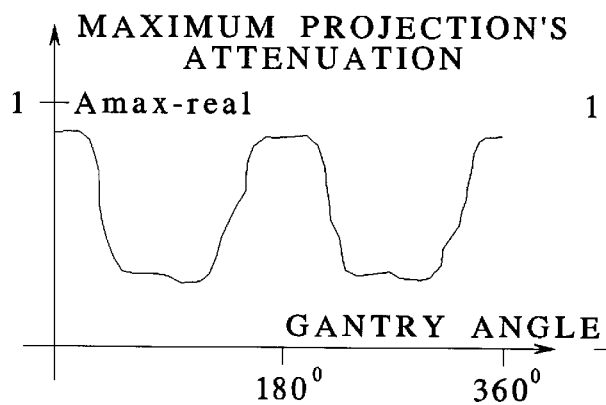
FIG. 4a is a typical attenuation profile acquired by a complete revolution of the gantry around the patient in the shoulder domain.
Figure 4B:
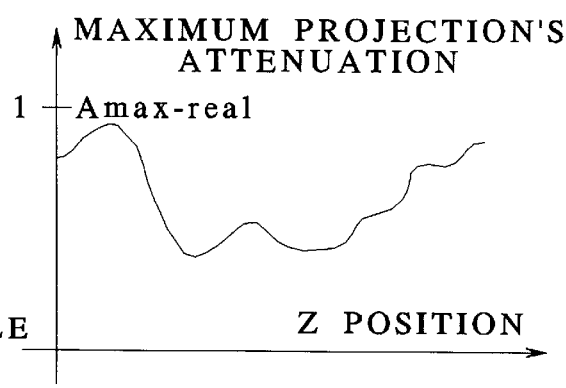
FIG. 4b is a attenuation profile for a tomogram.

In contrary to this the maximum attenuation established per projection as a function of gantry angle is called the attenuation profile. FIG. 4a shows a typical attenuation profile in the shoulder domain of the patient P. For the tomogram mode the attenuation profile shown in FIG. 4b represents the maximum attenuation per projection as a function of the patient's position along the z axis.

The intention of the inventive method is now to continuously predict an attenuation profile as for example shown in FIG. 4a on a value by value basis during the acquisition of patient projection data, with the predicted attenuation profile being, of course, at least approximately equal to the attenuation profile established on the basis of the detector voltage signals. Thus based on the predicted value of the maximum attenuation level for the respective next projection the power level of the x-ray tube 1 during the next projection is established and accordingly adjusted to adapt the x-ray power level to the anatomical domain of the patient to be examined by the next projection.

As mentioned the voltage signals produced by the 768 detectors per projection are sampled by the data measurement system 9. Using the high speed data link 10 the minimum detector 5 analyses the voltage signals received from the detectors of the bank of detectors 3 per projection. For every projection the minimum detector 5 analyses the detectors' voltage signals and determines the voltage value $U_{channel\_min}$ of the projection's minimum voltage signal. The minimum detector 5 establishes the voltage value $U_{monitor}$ of the voltage signal of the monitor detector, too, and submits both voltage values to the servo controller 6. The servo controller 6 uses the voltage value $U_{monitor}$ of the voltage signal of the monitor detector and the voltage value $U_{channel\_min}$ of the projection's minimum voltage signal in order to establish, i. e. by computing, the value $A_{max\_real}$ of the maximum attenuation of the projection:

$$A_{max\_real} = \frac{U_{channel\_min}}{U_{monitor}}.$$

This value is stored in a memory of the servo controller 6 for a prediction use to adjust the power level of the x-ray tube 1 only as high as necessary for the next projection. How many of such values $A_{max\_real}$ are to be stored for allowing is dependent on the method used for predicting the value of the maximum attenuation level for the next projection.

If a first order linear prediction method is used, the most expected attenuation level for the next projection will be found by the equation:

$$A_{max\_pred}(t) = A_{max\_real}(t-1),$$

wherein $A_{max\_real}(t-1)$ is the stored value of the maximum attenuation level of the foregoing projection based on the acquired patient projection data and $A_{max\_pred}(t)$ is the predicted value of the maximum attenuation level of the next projection. In this case there is always only one value $A_{max\_real}$ to be stored which will be overwritten by the value of the next established value $A_{max\_real+1}$. In general only as many established values of maximum attenuation levels of previous projections are stored in the memory of the servo controller 6 as are necessary for prediction the next value.

As in the case of the present preferred embodiment a second order linear prediction method is used to find the most expected attenuation level for the next projection as the prediction ensues according to the following equation wherein only the values of the maximum attenuation levels of the last two projection are stored for prediction:

$$A_{max\_pred}(t) = 2 A_{max\_real}(t-1) - A_{max\_real}(t-2),$$

wherein $A_{max\_pred}(t)$ is the predicted value of the maximum attenuation level of the next projection, $A_{max\_real}(t-1)$ is the established and stored value of the maximum attenuation level of the foregoing projection, and $A_{max\_real}(t-2)$ is the established and stored value of the maximum attenuation level of the last but one projection.

Figure 5:
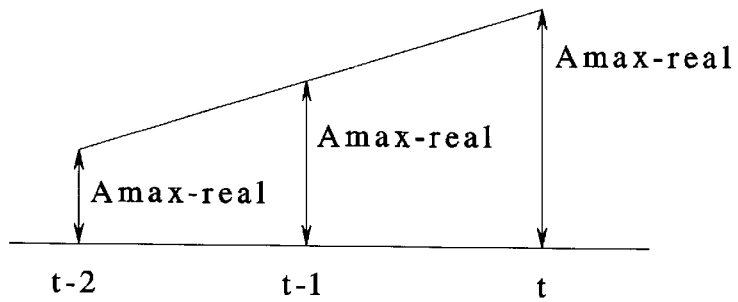
FIG. 5 is a graphic representation of the second order linear prediction method.

As the graphic representation of FIG. 5 shows, the second order linear prediction method uses the continuity of the attenuation profile's slope in order to estimate the most expected value of the maximum attenuation level for the next projection.

Different prediction methods eventually fit better for different scanning modes.

It should be noted that many other prediction methods can be used without departing from the spirit of this invention. Covered by the linear prediction theory are for example extrapolation algorithm based on polynomial approximation, Taylor series, spline interpolation, the continuity of the 1'st, 2'nd, . . . , n'th order derivate etc.

On the basis of the predicted value of the maximum attenuation level for the next projection the servo controller 6 now establishes, e. g. by computing, the power level of the x-ray tube 1 as high as necessary for the next projection according to the equation:

$$P_{est} = (A_{max\_pred}(t))^{-1} \rho,$$

if $(P_{est} > P_{max})$ then $P_{est} = P_{max}$ $\rho$ is the power density. The greater this parameter is, the greater is the power level of the x-ray tube 1 respectively the intensity of the x-rays reaching the detectors and the greater is the signal-to-noise ratio of the final image. This parameter is chosen as necessary or desired for reconstructing high quality cross section images of the patient out of the acquired patient projection data. $P_{max}$ is the maximum admissible power level for a projection. If the computed power level $P_{est}$ is higher than the maximum admissible power level $P_{max}$, the to be adjusted power level will be chosen equal to the maximal admissible power level $P_{max}$.

The respective established power level is adjusted by the power modulator 7 which receives an according signal from the servo controller 6 and controls the voltage on the gate electrode 12 of the x-ray tube 1. Modulation of the power level of the x-ray tube 1 thus modulates the x-ray dose applied to the patient P which is based on the prediction method substantially kept to a minimum. The use of an x-ray tube 1 comprising a gate electrode 12 is very advantageous, because the gate electrode 12 allows greater power swings in short time compared to conventional x-ray tubes. As studies with a homogenous, elliptical water phantom (40 cm×14 cm) shows the maximum power speed of the electrical power fed into the x-ray tube 1 recorded for a 750 ms rotation time of the gantry of a SOMATOM Plus 4 CT system comprising the x-ray tube 1 with the gate electrode 12 is 1,8 kW/ms or nearly 6 times larger as the power speed of a conventional x-ray tube without a gate electrode using the well known heater temperature modulation in order to indirectly adjust the anode current. The present used x-ray tube 1 comprising the gate electrode 12 works similar to an electronic triode. The heating current controls as usual the maximum available anode current, but the instantaneous anode current is controlled by the gate-cathode voltage. This allows a fast response, and thus a better power slew-rate. The accelerating high voltage electric field is always constant, which makes the energy of the electrons reaching the anode constant. That preserves the radiated spectrum of the x-ray tube 1.

Other test studies using the method according to the present invention were done with a record of real measured attenuation data from a patient with a SOMATOM Plus 4 CT system. The record contained 26382 projections over 25 rotations of the gantry around the patient. The CT system was configured as follow:

rotation time of the gantry: 0.75 sec high voltage of the x-ray tube: 120 kV x-ray tube current: 170 mA Z profile: SLIM width of the body slice of the patient: 8 mm spiral length: 122 mm anatomical domain of the patient: Mediastinum-Lung The real measured attenuation profile of the complete scan was compared with the predicted attenuation profile for the 26382 projections using the second order linear prediction method with the result that a maximum prediction error occurred from only 3.98% over the 26382 projections. This shows the very good performance of the method according to the present invention. Moreover this error can be considerably compensated by prescribing a greater power density $\rho$.

Compared with the conventional concept of power modulation of an x-ray tube the method of adaptive power modulation according to the present invention thus has three decisive advantages:

there is no need for a pre- or scout-scan, there are no more potentially errors due to the supposition that the attenuation profile is identical for two successive slices, and the prediction method works equally well for all common scanning modes: spiral, sequence, rotational and even tomogram.

The aforementioned operating modes are defined as follows:

(a) the spiral scanning mode—builds many successive cross section images of a patient by continuously moving the patient along the z axis at slow speed, with the gantry 4 simultaneously rotating.

(b) the sequence scanning mode—builds many cross section images of a patient by moving the patient P a step along the z axis after each complete rotation of the gantry 4.

(c) rotational scanning mode—is a transversal section through patient P perpendicular to the z axis. In this mode the patient P is fix and the gantry 4 rotates for at least 180° around the z axis taking many successive projections in order to gather enough attenuation data for the image reconstruction.

(d) the tomogram scanning mode—in this mode the gantry 4 remains stationary, generally with the x-ray tube 1 in a vertical or horizontal position and the patient table with the patient P moves continuously along the z axis through the fan shaped, stationary x-ray beam 2. Successive projections build up a two-dimensional image similar to the classic x-ray shadow image that represents the global body transparency to x-ray radiation.

It should be noted that, at the beginning of a scan which is performed according to the method of the present invention the image computer 11 issues a synchronization signal that instructs the servo controller 6 to reinitiate the prediction process. The initialization period of the prediction process will take a period of time, which equals the period of time necessary for performing the number of projections required for prediction. During the initialization period, the servo controller 6 uses the nominal power or uses a prediction with a shorter analysis depth for modulating the power level of the x-ray tube 1.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for adaptively modulating the power level of an x-ray tube of a computer tomography (CT) system for reducing an x-ray dose of an x-ray beam radiating through a patient and reaching detector means of said CT system during acquisition of projections of body slices of the patient, comprising the steps of:

establishing the value of the maximum attenuation level per projection out of the patient projection data acquired for the respective projection;

storing established values;

predicting the value of the maximum attenuation level for the next projection based on at least one of said stored values;

establishing, based on the respective predicted value, the power level of said x-ray tube for the next projection such that the minimum intensity of said x-ray beam reaching said detector means is greater than the quantum noise of said detector means; and adjusting the power level of said x-ray tube for the next projection according to said established power level of said x-ray tube.

2. The method as claimed in claim 1 wherein the step of predicting the value of the maximum attenuation level for the next projection is based on a first order linear prediction method in which the predicted value of the maximum attenuation level of the next projection is based on the established and stored value of the maximum attenuation level of the last projection.

3. The method as claimed in claim 2 wherein said first order linear prediction method is characterized by the equation $$A_{max\_pred}(t) = A_{max\_real}(t-1)$$

wherein $A_{max\_pred}(t)$ is the predicted value of the maximum attenuation level of the next projection, and $A_{max\_real}(t-1)$ is the established and stored value of the maximum attenuation level of the foregoing projection.

4. The method as claimed in claim 1 wherein the step of predicting the value of the maximum attenuation level for the next projection is based on a second order linear prediction method in which the predicted value of the maximum attenuation level of the next projection is based on the established and stored values of the maximum attenuation levels of the last two projections.

5. A method as claimed in claim 4 wherein said second order linear prediction method is characterized by the equation $$A_{max\_pred}(t) = 2 A_{max\_real}(t-1) - A_{max\_real}(t-2)$$

wherein $A_{max\_pred}(t)$ is the predicted value of the maximum attenuation level of the next projection, $A_{max\_real}(t-1)$ is the established and stored value of the maximum attenuation level of the foregoing projection, and $A_{max\_real}(t-2)$ is the established an stored value of the maximum attenuation level of the last but one projection.

6. The method as claimed in claim 1 wherein the step of establishing the power level of said x-ray tube is based on the predicted value of the maximum attenuation level of the next projection, a prescribed minimum power density (p) and a prescribed maximum admissible power level.

7. The method as claimed in claim 6 wherein the step of establishing the power level of said x-ray tube is characterized by the equation $$P_{est} = (A_{max\_pred}(t))^{-1} \rho$$

if $(P_{est} > P_{max})$ then $P_{est} = P_{max}$ wherein $P_{est}$ is the established power level of said x-ray tube which is to adjust, $P_{max}$ is the maximum admissible power level of said x-ray tube for a projection, $\rho$ is the power density, and $A_{max\_pred}(t)$ is the predicted value of the maximum attenuation level of the next projection.

8. The method as claimed in claim 1 wherein said x-ray tube comprises a voltage controlled electrode for adjusting the power level of said x-ray tube and said step of adjusting the power level of said x-ray tube comprises the step of controlling the voltage applied to said voltage controlled electrode such that the respective established power level is reached.

* * * * *